United States Patent [19]

O'Donnell

[11] Patent Number: 4,470,305

[45] Date of Patent: Sep. 11, 1984

[54] ANNULAR ARRAY USED AS A HORN TRANSDUCER

[75] Inventor: Matthew O'Donnell, Schenectady, N.Y.

[73] Assignee: General Electric Company, Schenectady, N.Y.

[21] Appl. No.: 423,871

[22] Filed: Sep. 27, 1982

[51] Int. Cl.³ ............................................. G01N 29/00
[52] U.S. Cl. ...................................... 73/626; 128/660; 367/153
[58] Field of Search ................. 73/625, 626, 642, 641; 128/660; 367/153, 103, 105, 150

[56] References Cited

U.S. PATENT DOCUMENTS

| 3,086,195 | 4/1963 | Halliday | 367/103 X |
| 4,044,273 | 8/1977 | Kanda | 367/150 X |
| 4,325,258 | 4/1982 | Foster | 73/642 |
| 4,339,952 | 7/1982 | Foster | 73/624 |

FOREIGN PATENT DOCUMENTS 681325 3/1964 Canada ................................ 367/103

OTHER PUBLICATIONS

M. Arditi, "An Annular Array System for High Resolution Breast Echography", Ultrasonic Imaging 4, 1-31 (1982).
"Focused Ultrasonic Transducer Design", Quarterly Progress Report, No. 98 (1970) Research Laboratory for Electronics, Massachusetts Institute of Technology.
D. R. Dietz, "Apodized Conical Focusing for Ultrasound Imaging", IEEE Trans. on Sonics and Ultrasonics, SU-29, 128-138, May 1982.

Primary Examiner—James L. Rowland
Assistant Examiner—James R. Giebel
Attorney, Agent, or Firm—Donald R. Campbell; James C. Davis, Jr.; Paul R. Webb, II

[57] ABSTRACT

Slowly tapering the cone angle as a function of distance along the cone results in a horn transducer that has a sharp focus in the near field and a large depth of field. The horn is simulated by time delaying the excitation pulse sequence to an annular array. An ultrasonic imaging system, particularly for contact B-scanning, uses an annular array to simulate both a horn transmitter and a fixed-focus receiver. This device has good resolution over a large depth of field and is easy to implement.

11 Claims, 14 Drawing Figures 4,470,305

ANNULAR ARRAY USED AS A HORN TRANSDUCER

BACKGROUND OF THE INVENTION

This invention relates to ultrasonic imaging and especially to a system having a horn transducer or simulated horn transmitter and to a method of imaging.

Conventional ultrasonic B-scan imaging systems use a single-element, fixed aperture transducer to form the beam. Because of this, these systems remain in focus over a limited depth of field. As an approach to focusing over a large depth of field, a number of authors have proposed using a conical transducer (see FIG. 1). However, for the physical dimensions that are consistent with contact B-scan imaging, the cone angle must be small (FIG. 2) to ensure that focusing is maintained to large depths. As a result, the focusing properties in the near field do not represent a significant improvement over a conventional B-scan transducer.

Variable focus annular arrays have also been proposed to increase the depth of field. These systems and those with conical transducers can be extremely complex and hence costly to manufacture.

SUMMARY OF THE INVENTION

A horn transducer, that is, a conical transducer whose cone angle varies linearly with length, enables focusing to be maintained at large depths without sacrificing the focusing properties in the near field. The horn permits focusing over a large depth of field using relatively small apertures. This transducer can be constructed as a single element, or can be simulated by appropriately time delaying the excitation pulse sequence to an annular array. Such a transducer for contact B-scanning has a diameter of about one inch and a typical depth of field from 2 to 20 centimeters.

A system architecture for use in B-scan ultrasonic imaging that is simple to implement yet results in enhanced resolution over a large depth of field, has an annular array transducer acting as both the transmitter and receiver. By choosing the delays to form a sharp horn taper, the transmitted beam pattern comes to a sharp focus in the near field and gradually weakens as a function of depth. On receive, the array is treated as an apodized, fixed-focus transducer spherically focused to a deep range. Such a transducer is sharply focused in the far field. Thus, when a horn transmitter is used in conjunction with a fixed-focus receiver, the two-way beam function is focused over a large depth of field. Focusing of received echoes is achieved electronically or mechanically by an acoustic lens placed on the array.

DETAILED DESCRIPTION OF THE INVENTION

Figure 1:
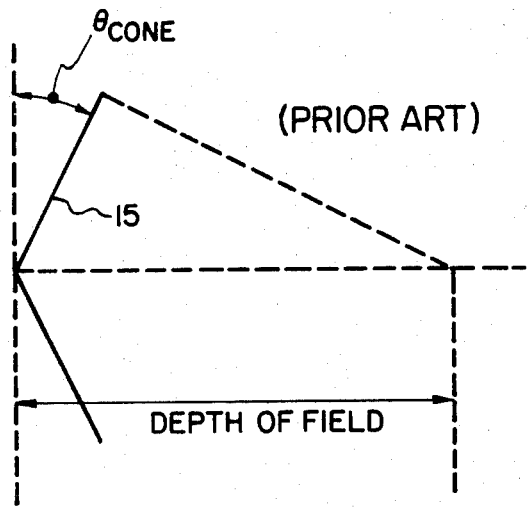
FIGS. 1 and 2 illustrate prior art large and small aperture conical transducers and focusing to large depths.
Figure 2:
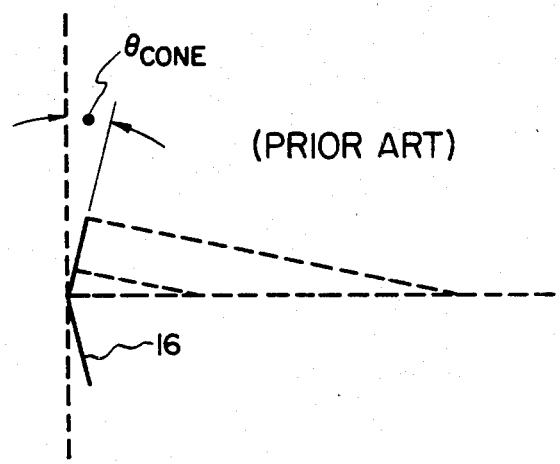

The cross section through a conical transducer 15 is illustrated in FIG. 1. This transducer can focus to a line extending from the cone tip to a point corresponding to the intersection of the cone axis and the normal to the cone edge. The maximum diameter of this transducer is fairly large such as might be used for scanning the breast. Because of the high sidelobe levels of conical transducers, such devices cannot be used in B-scan systems as pulse-echo transducers. That is, a conical transducer must be used solely as either the transmitter or the receiver. For contact B-scanning, commonly used in liver-abdominal imaging, the transducer is rubbed over the mid-section of the body and has a diameter of no more than 1 inch, and the desired depth of field is from 2 to 20 centimeters. FIG. 2 shows a small aperture conical transducer which has physical dimensions that are consistent with contact B-scanning imaging, but the cone angle must be small and not greater than about 5° to ensure focusing to a depth of 20 centimeters. As a result, the near field focusing of the small aperture cone is not too good.

Figure 3:
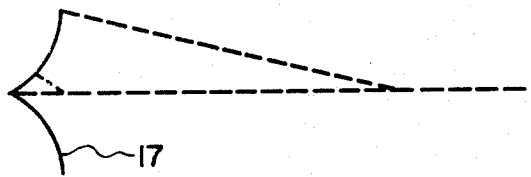
FIG. 3 is a sketch of a horn transducer focusing at different depths.
Figure 4:
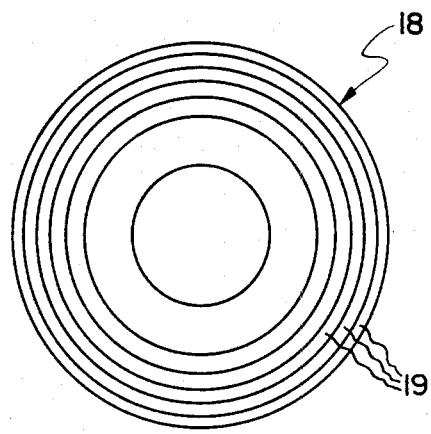
FIG. 4 depicts an annular array that has equal area rings.

This problem can be overcome by tapering the cone angle as a function of distance along the cone, resulting in a horn transducer. A diagram of a small aperture horn transducer 17 is presented in FIG. 3. By slowly tapering the cone angle to make a horn, focusing is maintained at large depths without sacrificing the focusing properties in the near field. The exact curvature of the horn can be chosen to optimize the beam function at all depths. The horn can be simulated by appropriate time delaying of the transmit pulse to each element of an annular array, or can be constructed as a single element. A simple illustration of an eight-ring annular array 18 is given in FIG. 4. The area of the individual annuli or rings 19 of this array is kept constant so that the radiation impedance of each element is constant. Thus, the annular array affords the possibility of using the same aperture to simulate a horn transmitter and a more conventional receiver.

Figure 5:
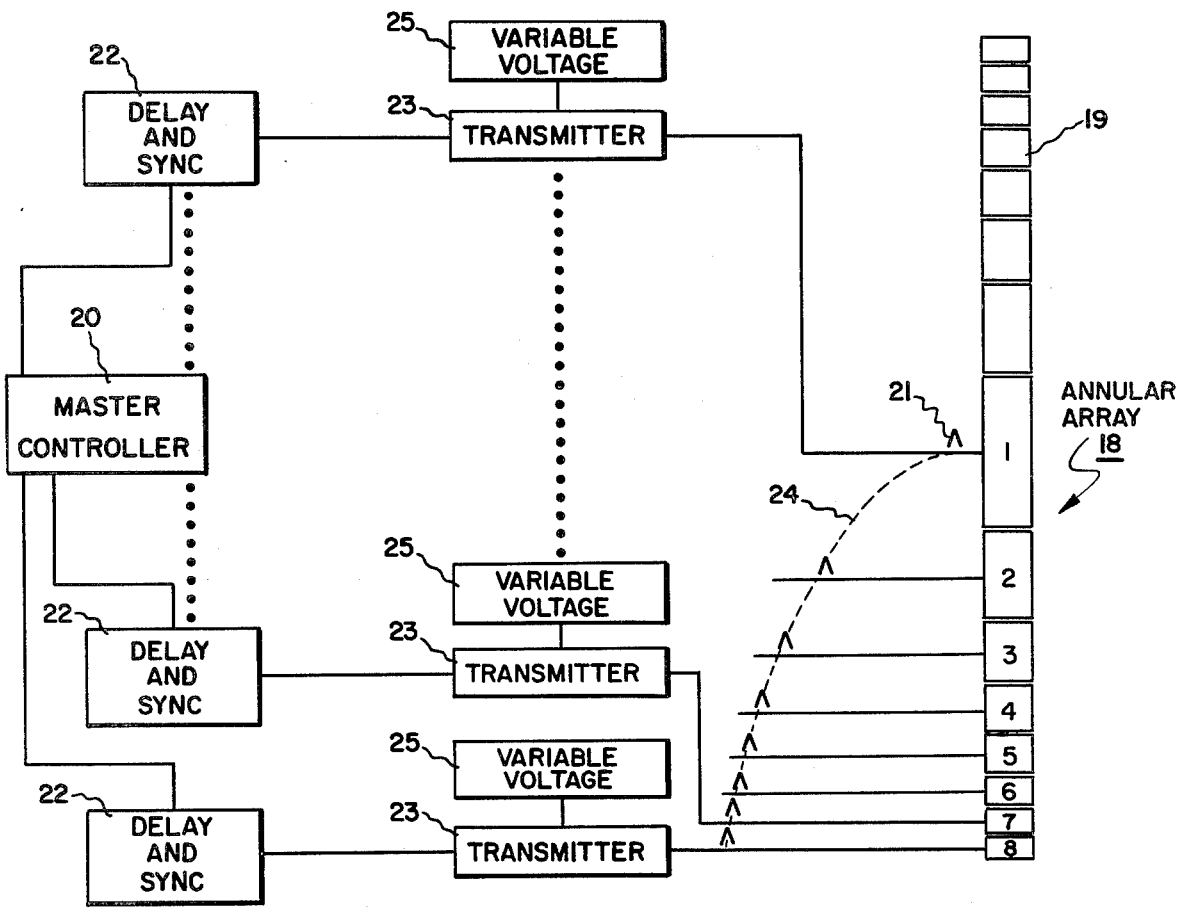
FIG. 5 is a block diagram of the transmitter section for the annular array and illustrates the time delayed excitation impulses to simulate a horn.

The block diagram of the transmitter section of a system which uses an annular array to simulate a horn transducer is shown in FIG. 5. A master controller 20 is provided, and the circuitry in the channel which applies an excitation pulse 21 to the first element includes delay and sync components 22 and the transmitter 23. These two units in the other channels are identified by the same numerals. Since the delay components of the transmitter section can be simple logic circuits, the cost of such a system is low. By choosing the delays to form a sharp horn taper, the transmitted beam pattern comes to a sharp focus in the near field and gradually weakens as a function of depth. Dashed line 24 illustrates a time delay sequence to simulate a horn. Variable voltage excitation can be obtained with this system if apodization of the aperture is desired. The amplitude of the excitation pulse is slightly less on the outside of the array in order to improve the far filed pattern; variable voltage circuits 25 change the voltage of the power supply of each transmitter for this purpose.

Figure 6:
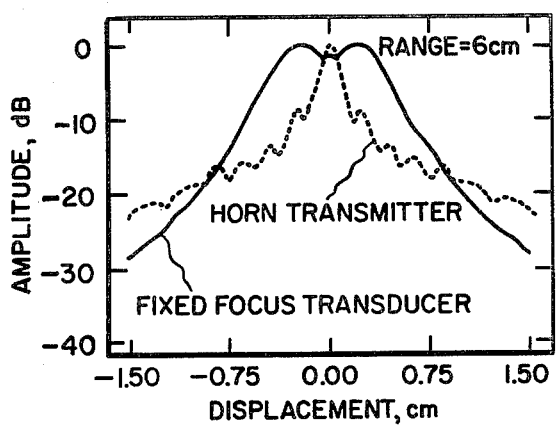
FIGS. 6 and 7 show the transmit beam patterns, respectively at short and long range, of a conventional circular fixed-focus transducer and an annular array used as a horn.

A computer model was developed to investigate the beam characteristics of broadband annular arrays and the model was tested against commerically available transducers. Using this computer model, the beam properties of an eight-ring annular array operating as a horn transmitter have been investigated. The center frequency of the transducer was chosen to be 3.0 MHz, with a bandwidth of 1.0 MHz. The aperture was 25.4 millimeters in diameter, this being the largest transducer that is useful for most contact B-scan applications, and segmented into eight equal area annuli. The time delay function was chosen so that the inner horn angle was approximately 50° and the outer horn angle was about 10°. Each element was excited with the same amplitude implulse, i.e., a uniform apodization function. These parameters do not necessarily represent optimal choices for a pulse-echo imaging system. In FIG. 6, the amplitude beam pattern of the horn transducer at a range of 6 centimeters is compared to the transmit (one way) beam pattern from a typical B-scan, fixed-focus transducer. All beam patterns are shown as a function of lateral displacement, rather than angle, to illustrate the B-scan imaging capabilities of each approach. The center frequency of the B-scan transducer was selected to be 3.0 MHz, with a bandwidth of 1.0 MHz. The transducer was 19.1 millimeters in diameter and was focused to a fixed depth of 15 centimeters.

Figure 7:
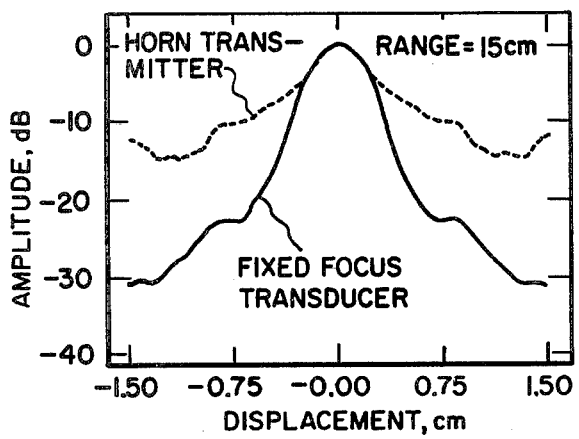

As is evident from FIG. 6, where the width of the central peak of the horn transmitter beam pattern is much less than that of the fixed-focus transducer, the near field focusing properties of the horn transducer are superior to those of the B-scan transducer. In FIG. 7, the focal properties of the horn transmitter are compared to those of the conventional B-scan transducer at a deeper range of 15 centimeters. The results presented in FIGS. 6 and 7 suggest that the horn transmitter produces a sharp focus in the near field that gradually weakens as a function of depth. In the focal region of the fixed-focus transducer, the beam pattern of the horn transmitter exhibits substantially higher sidelobes than the conventional transducer. However, the 6 dB beam width of the horn transmitter (6 dB down from maximum amplitude) is comparable to, or smaller than, the fixed-focus transducer to a depth of at least 25 centimeters. Therefore, the horn transmitter presents a high resolution technique that produces superior beam patterns in the very near field, but exhibits substantially elevated sidelobes as a function of depth.

The characteristics of the horn transmitter, that it comes to a sharp focus in the near field and gradually weakens and that is has elevated sidelobes as a function of depth, are in sharp contrast to an apodized transducer spherically focused to a deep range. By "apodized" it is meant that on receive the gains are varied from element to element along the array. Such a transducer exhibits a sharper focus as well as decreased sidelobe levels as a function of depth. Consequently, if a horn transmitter is used in conjunction with a fixed-focus receiver, then the two-way beam function can be focused over a large depth of field without substantially degrading the sidelobe levels. The ability to use an annular array as a fixed-focus receiver greatly reduces the complexity, and hence the cost, of the receiver electronics. The annular array transducer in the exemplary embodiment has a diameter of about 1 inch and, used as a horn transducer, a depth of field from 2 to 20 centimeters at 3.0 MHz. Used as a fixed-focus receiver, the array is focused at 15–20 centimeters.

Figure 8:
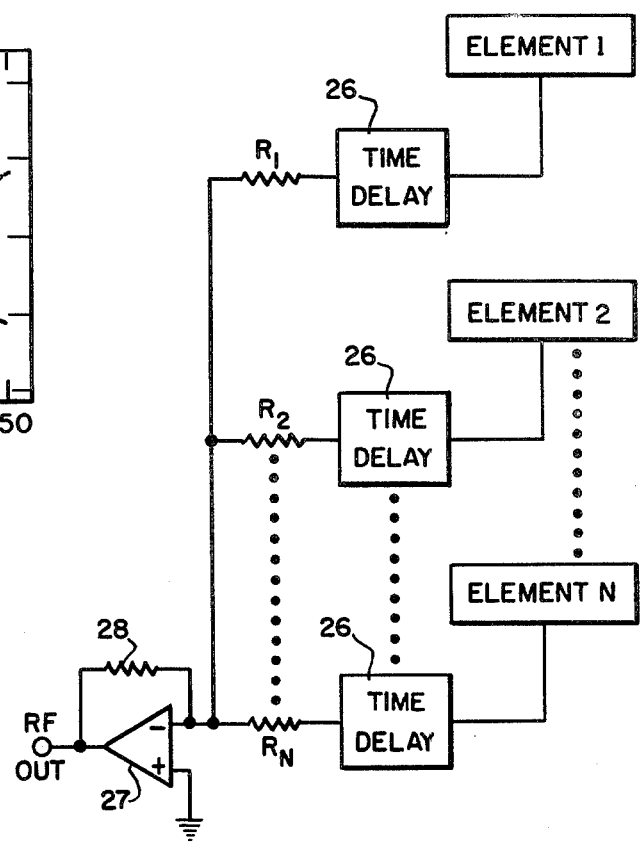
FIG. 8 is a diagram of the receiver section for an annular array used as an apodized, spherically focused transducer.

In FIG. 8, the block diagram of the front end electronics needed to use an annular array as an apodized, fixed-focus receiver is presented. The echo signal generated by the first transducer element passes through time delay circuitry 26, is attenuated by resistor $R_1$, and fed to the inverting input of an operational amplifier 27 which is connected as a summing amplifier and has a feedback resistor 28. The signals from all the channels 1 . . . N are summed and this is the RF output. The time delays shown in this figure are fixed delays chosen to spherically focus the annular array to a range close to the deepest depth to be imaged. The time delay function is a parabola in order to get a spherical focus. The resistor ladder is used to apodize the array to ensure that the sidelobe levels at the deeper ranges are not prohibitively large. Elements at the center of the array are assigned higher weights than elements at the outside. Because the receiver subsystem in FIG. 8 is so simple, it can be used as a preamplifier section so that the output of the array can serve as the input to a conventional B-scan imaging system.

Figure 9:
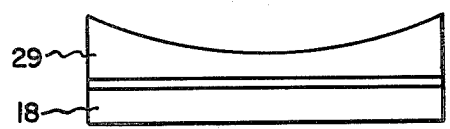
FIG. 9 illustrates an acoustic lens on the annular array.
Figure 10:
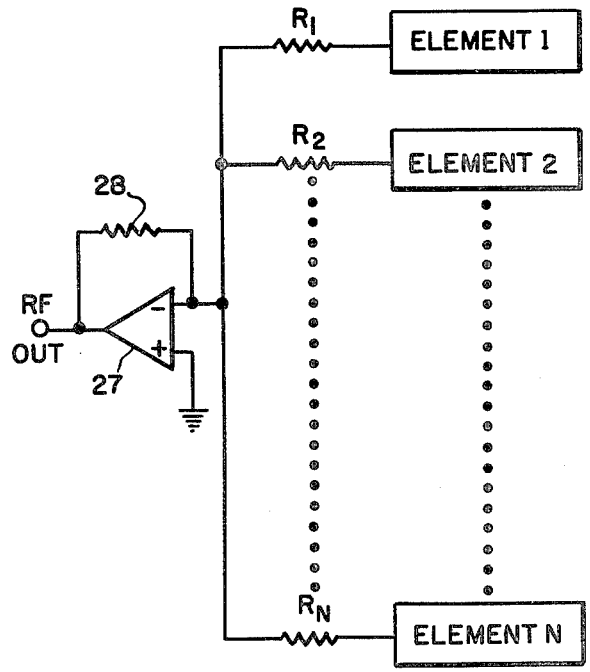
FIG. 10 shows the receiver section when echoes are mechanically focused as in FIG. 9.

Instead of electronically focusing the received echoes, they may be mechanically focused by an acoustic lens 29, FIG. 9, placed over the annular array 18. On transmission, the time delays of the excitation pulse sequence are compensated to account for passage through different lens thicknesses so that the annular array serves as a horn transducer. The receiver section now is as shown in FIG. 10, and the time delay circuitry is eliminated.

Figure 11:
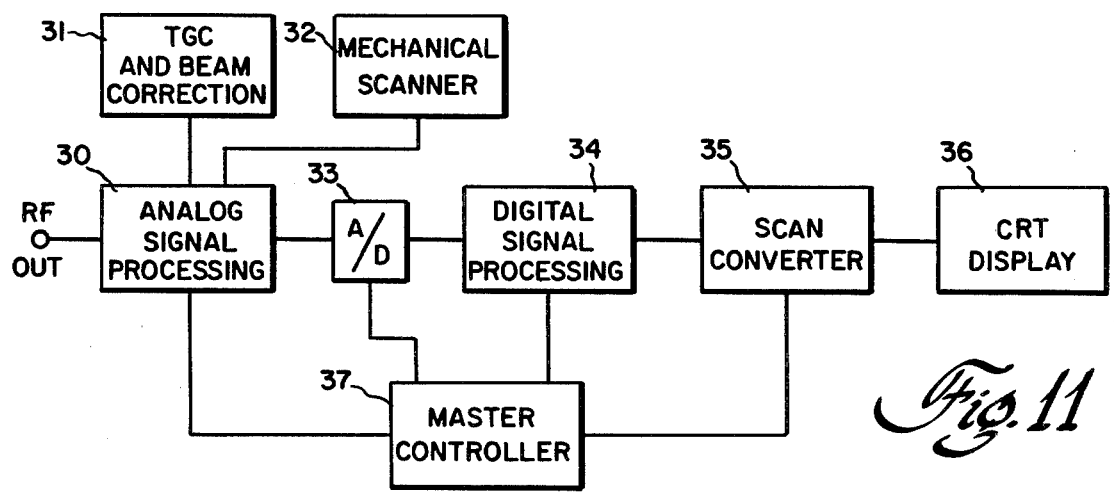
FIG. 11 is a block diagram of the B-scan imaging system.

The B-scan imaging system shown in block diagram form in FIG. 11 is conventional and is described only briefly. The transducer is scanned mechanically and is typically mounted on the end of an arm which may be locked in one plane; the x, y, and z positions are sensed by potentiometers in the arm. The summed and focused RF output signal is fed to analog signal processing circuitry 30 where it is envelope-detected, low pass filtered, etc., and converted to a video signal. A time gain compensation (TGC) correction is made for signal loss resulting from exponential attenuation of ultrasonic energy with increasing range, and a beam correction to compensate for amplitude variations away from the focal point. Information on the latter is stored in a memory 31. Transducer position information is also supplied from the mechanical scanner system 32. The processed signal is digitized in a high speed analog-to-digital converter 33 and hence sent to the digital signal processing unit 34 where the signal is scaled, averaged, smoothed, etc., as necessary. Image data is entered into a scan converter 35 and hence fed out to the cathode ray tube display device 36. These functions are coordinated by a master controller 37.

Figure 12:
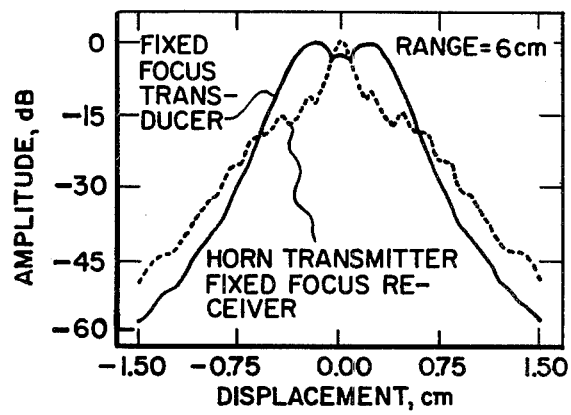
FIGS. 12 and 13 show the pluse-echo beam patterns, respectively at short and long range, for a conventional circular fixed-focus transducer and the annular array system.
Figure 13:
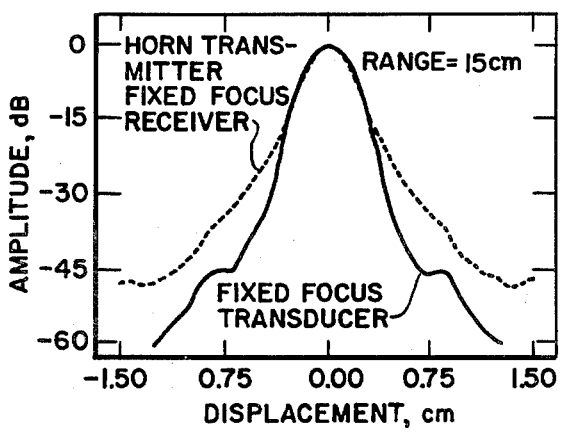
Figure 14:
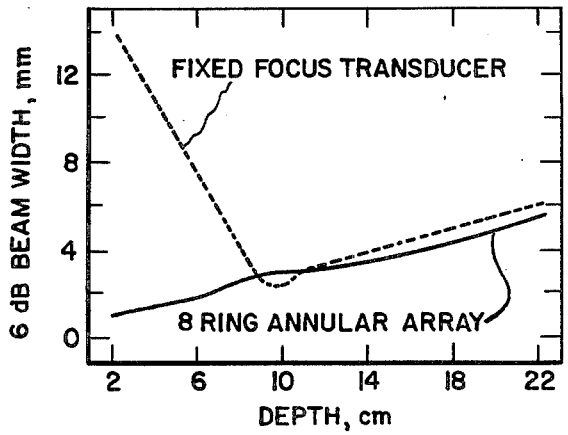
FIG. 14 illustrates graphically a comparison of the 6 dB beamwidth of a conventional circular fixed-focus transducer to the beamwidth of the annular array system.

In FIGS. 12 and 13, the pulse-echo beam functions from this system are compared to the pulse-echo beam functions from a typical B-scan, fixed-focus transducer at ranges of 6 centimeters and 15 centimeters. The properties of the B-scan transducer were the same as those previously described where it was mechanically focused to a depth of 15 centimeters. As is evident from these figures, the annular array system produced a tighter beam function at both ranges without greatly sacrificing sidelobe levels. FIG. 14 relates to a comparison of the 6 dB beamwidth of a fixed-focus transducer to the beamwidth of an annular array system. The width of the pulse-echo beam pattern 6 dB down from the maximum amplitude is plotted as a function of depth for both systems. As anticipated, the annular array system shows improved resolution over the range of 2 to 21 centimeters. It may be demonstrated that the sidelobe levels of the annular array system are generally higher than the conventional system, but do not seem prohibitive for most imaging applications.

Additional information is given in the inventor's publication "An Annular Array Imaging System for Contact B-scan Applications", Report No. 82CRD138, May 1982, General Electric Company, Corporate Research and Development, Schenectady, N.Y. 12345, the disclosure of which is incorporated herein by reference. (IEEE Transactions on Sonics and Ultrasonics, SU-29, pp. 331–338, November 1982 is the same in substance.)

While the invention has been particularly shown and described with reference to preferred embodiments thereof, it will be understood that various changes in form and details may be made therein without departing from the spirit and scope of the invention.

The invention claimed is:

1. An ultrasonic imaging system comprising:
   a multi-ring annular array for transmitting pulses of ultrasound into an object and receiving echoes;
   transmitter means for exciting said annular array to simulate a horn transducer, in which cone angle is slowly tapered from about 50° to 10° to make a horn, and have a line focus in the near field and a relatively large depth of field;
   means for using said annular array on receive as a fixed-focus transducer that is spherically focused close to the deepest range of said horn transducer; and
   means for forming an image.

2. The system of claim 1 wherein said annular array has equal area rings.

3. The system of claim 1 wherein said annular array has a diameter of no more than one inch and a depth of field of about 2 to 20 centimeters.

4. The system of claim 1 wherein said transmitter means generates a sequence of excitation pulses that are time delayed to simulate a horn and applied to the rings of said annular array.

5. The system of claim 1 wherein an acoustic lens on said annular array mechanically focuses received ultrasonic energy.

6. An ultrasonic imaging system for contact B-scan applications comprising:
   an annular array which has equal area rings and transmits pulses of ultrasound into an object and receives ultrasonic energy and generates echo signals;
   a transmitter section that supplies a sequence of excitation pulses to said annular array which are time delayed to simulate a horn transducer, in which cone angle is slowly tapered from about 50° to 10° to make a horn, having a sharp focus in the near field and a gradually weakening focus as a function of depth to the deepest depth to be imaged;
   a receiver section that configures said annular array as an apodized fixed-focus transducer that is spherically focused close to said deepest depth and which time delays and weights said echo signals accordingly and yields a summed signal; and
   means for processing said summed signal and producing an image.

7. The system of claim 6 wherein said annular array has a diameter of no more than one inch and depths of about 2 to 20 centimeters are imaged.

8. The system of claim 7 wherein said annular array has a minimum of 8 rings.

9. An ultrasonic imaging method comprising the steps of:
   transmitting pulses of ultrasound into an object by time delaying the excitation pulse sequence applied to the elements of an annular array so as to simulate a horn transducer, in which cone angle is slowly tapered from about 50° to 10° to make a horn, having a sharp focus in the near field and a gradually weakening focus to the deepest depth to be imaged;
   receiving echoes with said annular array and generating signals that are spherically focused close to said deepest depth and summed, whereby the system has good resolution over a large depth of field; and
   processing said summed signals and producing an image.

10. The method of claim 9 wherein said spherically focused signals are apodized to reduce sidelobe levels at deeper ranges.

11. The method of claim 10 wherein said excitation pulses have a variable amplitude, those applied to the outside of said annular array having a reduced amplitude compared to those applied to the inside, to improve the far field beam pattern.

* * * * *